(12) United States Patent
Chen (10) Patent No.: US 11,189,374 B2
(45) Date of Patent: Nov. 30, 2021

(54) METHOD AND SYSTEM FOR CALCULATING SUV NORMALIZATION COEFFICIENT IN A SPECT QUANTITATIVE TOMOGRAPHIC IMAGE

(71) Applicant: Atomical Medical Equipment (Fo Shan) Ltd., Guangdong (CN)

(72) Inventor: Si Chen, Guangdong (CN)

(73) Assignee: Atomical Medical Equipment (Fo Shan) Ltd., Foshan (CN)

( * ) Notice: Subject to any disclaimer, the term of this patent is extended or adjusted under 35 U.S.C. 154(b) by 114 days.

(21) Appl. No.: 16/842,712

(22) Filed: Apr. 7, 2020

(65) Prior Publication Data

US 2021/0065877 A1    Mar. 4, 2021

(30) Foreign Application Priority Data

Sep. 3, 2019  (CN) .......................... 201910827035.5

(51) Int. Cl.
| | |
|---|---|
| G06K 9/00 | (2006.01) |
| G16H 30/20 | (2018.01) |
| G06T 7/11 | (2017.01) |
| G06N 3/02 | (2006.01) |
| G06T 7/00 | (2017.01) |

(52) U.S. Cl.
CPC .............. *G16H 30/20* (2018.01); *G06N 3/02* (2013.01); *G06T 7/0012* (2013.01); *G06T 7/11* (2017.01); *G06T 2207/10108* (2013.01); *G06T 2207/20081* (2013.01); *G06T 2207/20084* (2013.01)

(58) Field of Classification Search
CPC ..................................................... G16H 30/20
See application file for complete search history.

(56) References Cited

U.S. PATENT DOCUMENTS

| | | | | |
|---|---|---|---|---|
| 10,304,183 | B2* | 5/2019 | Mikhno | ................. G06T 15/08 |
| 2007/0081712 | A1* | 4/2007 | Huang | ..................... G06T 7/33 |
| | | | | 382/128 |
| 2011/0103669 | A1* | 5/2011 | Michel | .................. G06T 11/005 |
| | | | | 382/131 |
| 2014/0365137 | A1* | 12/2014 | Burger | ................. A61B 6/5217 |
| | | | | 702/19 |

FOREIGN PATENT DOCUMENTS

| | | |
|---|---|---|
| CN | 102920537 A | 2/2013 |
| CN | 102741707 B | 4/2014 |
| CN | 110599472 A | 12/2019 |

\* cited by examiner

*Primary Examiner* — Hadi Akhavannik (57) ABSTRACT

The present invention discloses a method and system for calculating SUV normalization coefficient in a SPECT quantitative tomographic image, comprises the following steps: a) averaging the anterior plain film image and posterior plain film image obtained by performing plain film scanning on a subject's whole body to get an average image, from which the area corresponding to the radioactive uptake site in the subject is segmented, b) correcting attenuation coefficient of human body, detection efficiency and acquisition time for each pixel value in the effective radioactive uptake area within said average image, c) averaging all the effective radioactive uptake area pointed at by said quantitative two-dimensional radioactive uptake activity image obtained in step b, and performing volume normalization and decay time correction to figure out the average radiopharmaceutical activity concentration absorbed in the subject.

10 Claims, 6 Drawing Sheets averaging the anterior plain film image and posterior plain film image obtained by performing plain film scanning on a subject's whole body to get an average image, from which the area corresponding to the radioactive uptake site in the subject is segmented correcting attenuation coefficient of human body, detection efficiency and acquisition time for each pixel value in the effective radioactive uptake area within average image, and calculating the average radioactive uptake activity of the human body part corresponding to each pixel in the anteroposterior direction, further to figure out the quantitative two-dimensional radioactive uptake activity image after averaging each part of the human body corresponding to the average image in the anteroposterior direction averaging all the effective radioactive uptake area pointed at by said quantitative two-dimensional radioactive uptake activity, and performing volume normalization and decay time correction to figure out the average radiopharmaceutical activity concentration absorbed in the subject, to be used to calculate the standard uptake value of a SPETOMOGRAPHIC quantitative tomography image.

METHOD AND SYSTEM FOR CALCULATING SUV NORMALIZATION COEFFICIENT IN A SPECT QUANTITATIVE TOMOGRAPHIC IMAGE

CROSS-REFERENCE TO RELATED APPLICATIONS

This application claims the benefit of priority from Chinese Patent Application No. 201910827035.5, filed on Sep. 3, 2019. The content of the aforementioned application, including any intervening amendments thereto, is incorporated herein by reference in its entirety.

TECHNICAL FIELD

The present invention relates to the technical field of nuclear medicine imaging, and more specifically to a method and system for calculating SUV normalization coefficient in a SPECT quantitative tomographic image.

BACKGROUND ART

The standardized uptake value (SUV) is a semi-quantitative indicator commonly used in the positron emission tomography (PET) in the tumor image analysis, and specifically refers to the ratio of the radioactivity concentration of the imaging agents absorbed by local tissues to the average radioactivity concentration injected systemically. The concentration ratio is shown in the following formula:

$$SUV = \frac{r}{(a'/w)}$$

wherein, r is the activity concentration of the radiopharmaceuticals (Unit: Bq/ml) absorbed in a certain region of interest (ROI) revealed by the quantitative PET image, and a' is the activity at imaging time point (Unit: Bq), converted with a decaytime from the total radiopharmaceutical activity injected into the subject, and w is the subject's weight (Unit: g). Assuming that the density of the human body is approximately equal to the density of water 1 g/ml, the value of w is approximately equal to the volume of the radiopharmaceutical distribution in the subject, so a'/w is approximately equal to the average activity concentration of the radiopharmaceutical in the subject, which is the normalization coefficient of the standardized uptake value (SUV).

Although the SUV is widely used in clinical practice at home and abroad as a quantitative index for image analysis, its accuracy and precision are also affected by many factors. In terms of image quantification methods, that is, the measurement of r will be affected by factors such as the size of the lesion, the outline of the region of interest, the equipment performance, the imaging conditions, the acquisition mode, the reconstruction algorithm, the operation method (such as outlining the size of ROI), and the attenuation correction. The accuracy of the average activity concentration (that is, the normalization coefficient of the SUV) is affected by two aspects of the subject's own factors and the operation process. The subject's own factors include the subject's fat content, blood glucose level, clearance rate of the 18F-FDG in the blood circulation, urination and the like, and other factors in the operation process include the measurement accuracy of the medicamentous injection dose, whether it is residual, and the accuracy of time recording and the like.

In the $21^{st}$ century, with the advancement of PET and SPECT technology, especially as the all-in-one machines with the PET/CT and the SPECT/CT is widely used in clinical practice, the iterative image reconstruction algorithm software including modules such as attenuation correction, scattering correction, and resolution restoration has gradually become the standard configuration of clinical equipment, so the quantitative imaging performance of the PET and the SPECT has been significantly improved, and the accuracy and precision of image quantification have reached a higher level. At present, the main problems that still exist at the level of image quantification methods rest with the consistency of equipment from different manufacturers and the quality control (periodical calibration) during the use of equipment. At the same time, the factors such as the subject's own factors and the medical staffs preparations before injecting the radiopharmaceuticals and forming the images of subjects have increasingly become the main factors potentially affecting the accuracy of the SUV. Some studies have shown that the residual radioactive dose in the needle can averagely reach 2% of the total dose after injection, and in individual cases can reach more than 20%. This part of the residual dose, if not measured and corrected, will bring some corresponding errors to the average activity concentration a'/w (that is, the normalization coefficient of the SUV) and the calculation of the SUV. The other studies have shown that the dose of the radiopharmaceuticals excreted in the urine of PET subjects can account for 5.7% to 15.2% of the injected dose. If this part of the dose cannot be accurately corrected in the SUV calculation, it will cause quantitative standards between different patients to have differentiation, and brings certain errors to the evaluation of multiple imaging results of the same patient.

The above-mentioned subject's factors and medical staff's operating factors affecting the quantitative accuracy of the PET imaging SUV values are also present in SPECT quantitative imaging, and may even be more prominent. An example is as follows. The injected medicant remains on the patient's body surface. When a $^{99m}$Tc-MDP bone scan is performed, the interval between injection and scan is about 2 hours, and the subjects will vary in urination. Some new SPECT tumor-imaging radiopharmaceuticals, such as $^{99m}$Tc-3PRGD2, are mainly eliminated from the body by the urinary system. Therefore, the medicant rapidly accumulates high radioactivity in the urine and requires urination in about 1 hour. The above situations will greatly affect the calculation of the average concentration of the radiopharmaceuticals absorbed in the subject (that is, the normalization coefficient of the SUV) by using the ratio of the injected dose to the weight of the subject, and then affect the accuracy of calculating the SUV value.

In the tumor imaging commonly used in clinical practice, the SPECT acquisition procedure is usually different from the PET. The PET usually performs a multi-positional 3D tomographic scan directly on the subject, and then does split joint to obtain a systemic 3D tomographic image. But the SPECT usually performs plain film scanning on the subject's whole body first to obtain the systemic plain film images at A-P position, and then is determined by a doctor. A local tomographic scan is performed, according to the clinical needs, to obtain a local 3D tomographic image, that is, the SPECT tomographic image. The calculation of the SUV value is aimed at this local 3D tomographic image. At present, all the prevailing SPECT/CT all-in-one devices in clinical applications provide quantitative reconstruction algorithm software, which can be used to reconstruct quantitative tomographic images with a pixel value unit of Bq/ml.

However, due to the limitation of actual needs and working conditions, most of the SPECT tumor imaging does not accurately record the subject's medicamentous injection dose and weigh in clinical practice. Therefore, in terms of feasibility, it is limited to some extent that the method similar to the PET imaging is used to measure the average activity concentration of the medicant injected into the subject's body and further calculate the SUV value.

SUMMARY

Technical Problems

It is an object of the invention to provide a method and system for calculating SUV normalization coefficient in a SPETOMOGRAPHIC quantitative tomographic image, in order to solve the problem that the conventional method based on the injection dose and patient weight is inaccurate, because of inaccurate injection dose, lack of related records, patient's urination before imaging, etc. in SPETOMOGRAPHIC imaging, and results in the inability to accurately calculate the SUV value of the region of interest in the SPETOMOGRAPHIC tomographic image.

Solutions to Problems

Technical Solutions

This object is achieved by a method for calculating SUV normalization coefficient in a SPETOMOGRAPHIC quantitative tomographic image, comprising the following steps:

a) averaging the anterior plain film image and posterior plain film image obtained by performing plain film scanning on a subject's whole body to get an average image, from which the area corresponding to the radioactive uptake site in the subject is segmented, and defined as an effective radioactive uptake area, b) correcting attenuation coefficient of human body, detection efficiency and acquisition time for each pixel value in the effective radioactive uptake area within said average image, and calculating the average radioactive uptake activity of the human body part corresponding to each pixel in the anteroposterior direction, further to figure out the quantitative two-dimensional radioactive uptake activity image after averaging each part of the human body corresponding to the average image in the anteroposterior direction, wherein said attenuation coefficient of human body is an average linear attenuation coefficient of the part of human body corresponding to a pixel value, c) averaging all the effective radioactive uptake area pointed at by said quantitative two-dimensional radioactive uptake activity image obtained in step b, and performing volume normalization and decay time correction to figure out the average radiopharmaceutical activity concentration absorbed in the subject, which is a SUV normalization coefficient used to calculate a SPETOMOGRAPHIC quantitative tomography image.

Preferably, in step a the average image is obtained by calculating a geometric average value or an arithmetic average value of pixel values of pixels corresponding to all spatial positions in said anterior plain film image and posterior plain film image.

Preferably, the obtaining of the effective radioactive uptake area in step a specifically comprises:

first segmenting all areas corresponding to the radioactive uptake site of human body in said average image by an image segmentation method based on thresholds or texture features, then detecting a pre-defined invalid radioactive uptake area in said average image by a deep-learning or machine-learning algorithm, next segmenting all the detected invalid radioactive uptake areas by a level set segmentation method or a deep-learning-based segmentation method, and setting a pixel value corresponding to said invalid radioactive uptake area to 0 or an average value of surrounding areas in said average image, thereby obtaining the effective radioactive uptake region in said average image.

Preferably, the obtaining of said quantitative two-dimensional radioactive uptake activity image in step b specifically comprises:

b1) correcting the attenuation coefficient of human body, wherein a SPETOMOGRAPHIC systemic plain film image and a local TOMOGRAPHIC tomographic image of a subject, and a three-dimensional attenuation coefficient chart based on digital human model are applied to jointly perform image registration, and then the average linear attenuation coefficient corresponding to all effective radioactive uptake areas in the subject is obtained, b2) correcting the detection efficiency, wherein types of the SPETOMOGRAPHIC acquisition device and collimator are read from a Dicom data file header information of said SPETOMOGRAPHIC systemic plain film image, and used them to calculate gamma photon detection efficiency, and then the pixel value of the SPETOMOGRAPHIC systemic plain film image is divided by the gamma photon detection efficiency, to figure out the number of gamma photons cumulatively emitted from corresponding parts of human body, b3) performing normalization correction of acquisition time, wherein acquisition time of the systemic plain film image and the SPETOMOGRAPHIC tomographic image from the Dicom data file header information of the subject's SPETOMOGRAPHIC systemic plain film image is read, then a normalization calculation is performed on the number of gamma photons obtained in step b2, and the quantitative two-dimensional radioactive uptake activity image is figured out after averaging the three-dimensional spatial distribution of the radioactive uptake activity of each part of the human body corresponding to said average image in the anteroposterior direction.

Preferably, in step b3, assuming that the radiopharmaceuticals and attenuation coefficients in different parts of human body are evenly distributed in the anteroposterior direction, a mathematical model of SPETOMOGRAPHIC projection data acquisition is established in accordance with $$P_i = t * s_{col} * b_i * \exp\left(-\frac{\mu_i d}{2}\right) * \sum_{j=0}^{n_i-1} \exp(-\mu_i j d),$$

$$= t * s_{col} * b_i * \exp\left(-\frac{\mu_i d}{2}\right) \frac{1 - \exp(-\mu_i n_i d)}{1 - \exp(-\mu_i d)}$$

wherein, $P_i$, $i \in I_0$ is the pixel value of all pixels included in the effective radioactive uptake area $I_0$ in said average image, and i is the pixel index number, and d is the side length of the graphic pixel of the SPETOMOGRAPHIC systemic plain film image, read from the Dicom data file header information of the SPETOMOGRAPHIC systemic plain film image, and $b_i$ is the average radioactive uptake activity of the radioactive uptake site of human body corresponding to the pixels i in said average image in the anteroposterior direction, and $s_{col}$ is the detector sensitivity, $s_{col}$ is obtained from the product parameter description table of the SPETOMOGRAPHIC acquisition device and collimator, and t is the equivalent acquisition time read from the Dicom data file header information of the SPETOMOGRAPHIC systemic plain film image, and $\mu_i$ is the average linear attenuation coefficient of the radioactive uptake site of human body corresponding to the pixel i in the average image in the anteroposterior direction, and $n_i$ is the voxel number obtained by one-dimensional discretization of the radioactive uptake site of human body corresponding to the pixel i in the average image in the anteroposterior direction with the side length d as the sampling size, that is what the thickness of the radioactive uptake site of human body in the anteroposterior direction is divided by the side length d to figure out.

Preferably, in step b3 the estimated value of $\mu_i$ and $n_i$ in said mathematical model of SPETOMOGRAPHIC projection data acquisition is obtained by step b1, specifically comprising:

for the part of human body with the local TOMOGRAPHIC tomographic image, converting the local TOMOGRAPHIC tomographic image of the part of human body into the attenuation coefficient chart corresponding to 140 keV gamma photons for the SPETOMOGRAPHIC imaging by bilinear transformation, then figuring out the average linear attenuation coefficient $\mu_i$, voxel number $n_i$, and anteroposterior cumulative attenuation coefficient $\exp(-\mu_i n_i d)$ of the effective radioactive uptake area covered by and according to said attenuation coefficient chart, for the part of human body lacking the local TOMOGRAPHIC tomographic image, performing image registration on the SPETOMOGRAPHIC systemic plain film image and the three-dimensional attenuation coefficient chart based on digital human model to obtain a plain film chart of anteroposterior cumulative attenuation coefficient, that is $\exp(-\mu_i n_i d)$, $i \in I_0$, then performing 3D registration on the local TOMOGRAPHIC tomographic image of the subject and the three-dimensional attenuation coefficient chart based on digital human model to obtain the anatomical part that best matches the local TOMOGRAPHIC tomographic image of the subject, thereby obtaining an anteroposterior thickness proportionality factor of the mathematical model of the SPETOMOGRAPHIC projection data acquisition to the corresponding parts of the subject, then applying the anteroposterior thickness proportionality factor to the anatomical part that is not covered by the local TOMOGRAPHIC tomographic image of the subject in the three-dimensional digital human model, thereby obtaining an estimated thickness value of each part of the subject's whole body, that is, $n_i d$ $i \in I_0$, thus, figuring out the average linear attenuation coefficient $\mu_i$ of all effective radioactive uptake areas, in said step b3 according to the mathematical model of the SPETOMOGRAPHIC projection data acquisition, obtaining the average radioactive uptake activity $b_i$ of the radioactive uptake site of human body corresponding to the pixels i in the average image in the anteroposterior direction in accordance with $$b_i = P_i * \exp\left(\frac{\mu_i d}{2}\right) \frac{1 - \exp(-\mu_i d)}{(1 - \exp(-\mu_i n_i d)) * t * s_{col}}.$$

Preferably, said step c specifically comprises:

c1) averaging all the effective radioactive uptake area pointed at by said quantitative two-dimensional radioactive uptake activity image obtained in step b, and performing volume normalization by using the pixel size contained in the Dicom data file header information of the SPETOMOGRAPHIC systemic plain film image to obtain the average radioactivity concentration in human body in the intermediate instant of the acquisition of the SPETOMOGRAPHIC systemic plain film image.

c2) performing decay time correction according to the acquisition time interval in the SPETOMOGRAPHIC tomographic image data of the subject and the Dicom data file header information of the SPETOMOGRAPHIC systemic plain film image to figure out the average radiopharmaceutical activity concentration absorbed in the subject in accordance with $$b = \frac{\Sigma_{i \in I_0} b_i n_i}{\Sigma_{i \in I_0} n_i} \frac{\exp[-\lambda(t_2 - t_1)]}{d^2},$$

where $t_1$ is the intermediate instant of the acquisition of the SPETOMOGRAPHIC systemic plain film image, $t_2$ is the intermediate instant of the acquisition of the SPETOMOGRAPHIC tomographic image, and $\lambda$ is the radionuclide decay coefficient, c3) obtaining the average radiopharmaceutical activity concentration b that is normalization coefficient used to calculate the standard uptake value of the SPETOMOGRAPHIC quantitative tomographic image, and using said average radiopharmaceutical activity concentration b for the normalization of the SPETOMOGRAPHIC quantitative tomography physical image to obtain the SPETOMOGRAPHIC quantitative tomographic image with the SUV value as the dimension, and calculating and evaluating the SUV value of any region of interest in said SPETOMOGRAPHIC quantitative tomographic image.

Preferably, a system for calculating SUV normalization coefficient in a SPETOMOGRAPHIC quantitative tomographic image, comprising:

a module for calculating an effective radioactive uptake area, which is used to average the anterior plain film image and posterior plain film image obtained by performing plain film scanning on a subject's whole body to get an average image, from which the area corresponding to the radioactive uptake site in the subject is segmented, and defined as an effective radioactive uptake area, a module for calculating a quantitative two-dimensional radioactive uptake activity image, which is used to correct attenuation coefficient of human body, detection efficiency and acquisition time for each pixel value in the effective radioactive uptake area within said average image, and calculate the average radioactive uptake activity of the human body part corresponding to each pixel in the anteroposterior direction, further to figure out the quantitative two-dimensional radioactive uptake activity image after averaging each part of the human body corresponding to the average image in the anteroposterior direction, wherein said attenuation coefficient of human body is an average linear attenuation coefficient of the part of human body corresponding to a pixel value, and a module for calculating an average radiopharmaceutical activity concentration, which is used to average all the effective radioactive uptake area pointed at by said quantitative two-dimensional radioactive uptake activity image, and perform volume normalization and decay time correction to figure out the average radiopharmaceutical activity concentration absorbed in the subject, which is a SUV normalization coefficient used to calculate a SPETOMO-GRAPHIC quantitative tomography image.

Preferably, said module for calculating an effective radioactive uptake area comprises:

a first submodule, which is used to segment all areas corresponding to the radioactive uptake site of human body in said average image by an image segmentation method based on thresholds or texture features, a second submodule, which is used to detect a pre-defined invalid radioactive uptake area in said average image by a deep-learning or machine-learning algorithm, and a third submodule, which is used to segment all the detected invalid radioactive uptake areas by a level set segmentation method or a deep-learning-based segmentation method, and set a pixel value corresponding to said invalid radioactive uptake area to 0 or an average value of surrounding areas in said average image, thereby obtain the effective radioactive uptake region in said average image.

Preferably, said module for calculating a quantitative two-dimensional radioactive uptake activity image comprises:

a fourth submodule for correcting the attenuation coefficient of human body, wherein a SPETOMOGRAPHIC systemic plain film image and a local TOMOGRAPHIC tomographic image of a subject, and a three-dimensional attenuation coefficient chart based on digital human model are applied to jointly perform image registration, and then the average linear attenuation coefficient corresponding to all effective radioactive uptake areas in the subject is obtained, a fifth submodule for correcting the detection efficiency, wherein types of the SPETOMOGRAPHIC acquisition device and collimator are read from a Dicom data file header information of said SPETOMOGRAPHIC systemic plain film image, and used them to calculate gamma photon detection efficiency, and then the pixel value of the SPETOMOGRAPHIC systemic plain film image is divided by the gamma photon detection efficiency, to figure out the number of gamma photons cumulatively emitted from corresponding parts of human body, and a sixth submodule for performing normalization correction of acquisition time, wherein acquisition time of the systemic plain film image and the SPETOMOGRAPHIC tomographic image from the Dicom data file header information of the subject's SPETOMOGRAPHIC systemic plain film image is read, then a normalization calculation is performed on the number of gamma photons obtained, and the quantitative two-dimensional radioactive uptake activity image is figured out after averaging the three-dimensional spatial distribution of the radioactive uptake activity of each part of the human body corresponding to said average image in the anteroposterior direction.

Compared with the existing calculation methods based on medicamentous injection dose and weight, there are two advantages in said method for calculating SUV normalization coefficient in a SPETOMOGRAPHIC quantitative tomographic image.

In terms of accuracy, the present invention avoids errors in operating and recording the drug injection dose from affecting the accuracy of the SUV value calculation, and at the same time, it can correct and compensate for some special factors such as bladder uptake, radioactive contamination of body surface, at the level of plain film images according to clinical use habits and the actual situation of patients. For example, a predefined area of invalid radioactive uptake is segmented to improve the accuracy of the SUV normalization coefficient calculation, further enhance the accuracy of the SUV value calculation.

In terms of reliability, since all the input data of the algorithm of the present invention are derived from the Dicom image data and file header information output by the SPETOMOGRAPHIC device, it can be read and operated fully automatically, without the need for manual operation and keeping separate records, so it has higher reliability and better traceability.

BRIEF DESCRIPTION OF THE DRAWINGS

Description of the Drawings

The present invention will be further described in detail below with reference to the figures, but the protection scope of the present invention is not limited to the figures.

FIG. 2(a) is an anterior and posterior systemic plain film image, FIG. 2(b) is an average image, and FIG. 2(c) is a diagram of the entire radioactive uptake area of human body, FIG. 3(a) is a diagram of an area of invalid radioactive uptake, FIG. 3(b) is an example diagram of a detected area of invalid radioactive uptake, and FIG. 3(c) is an example diagram of segmenting an area of invalid radioactive uptake, FIG. 6(a) to FIG. 6(g) are systemic three-dimensional attenuation coefficient charts using a digital human model, and FIGS. 6(h) to 6(j) are local TOMOGRAPHIC tomographic images.

OPTIMAL EMBODIMENTS FOR IMPLEMENTING THE INVENTION

Optimal Embodiments of the Invention

The technical solutions of the present invention will be further described in detail below with reference to the figures and specific embodiments.

Embodiment 1

Figure 1:
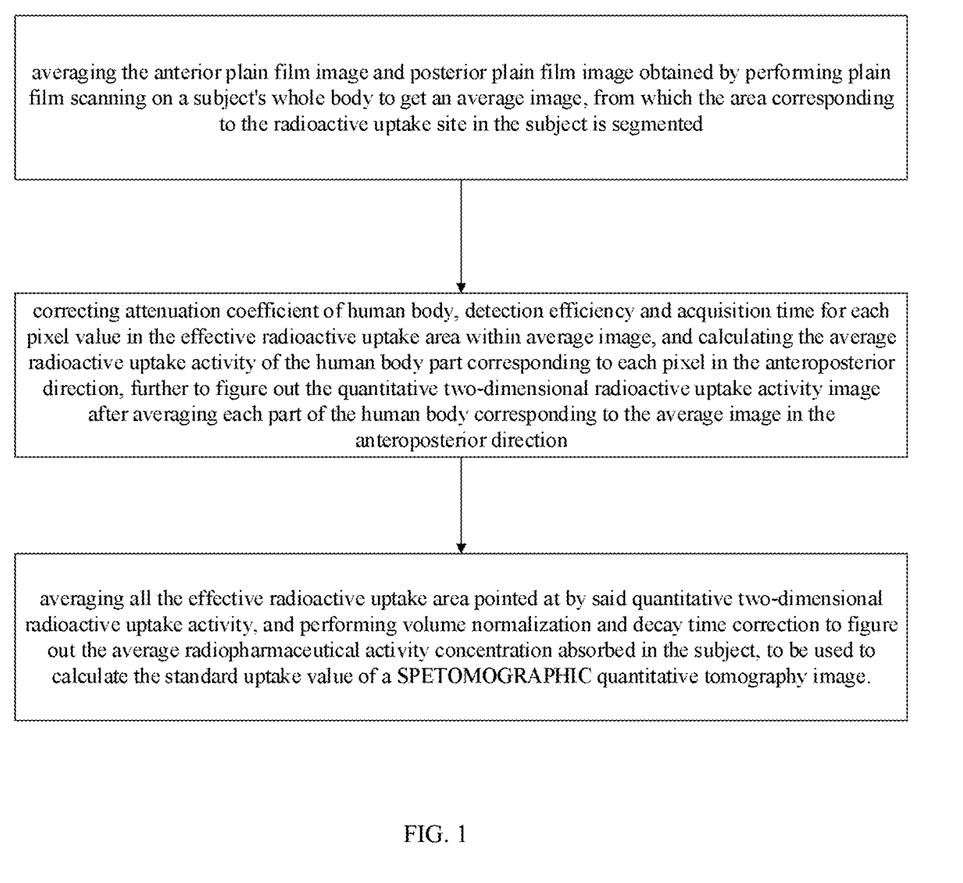
FIG. 1 is a schematic diagram of a calculation process of one embodiment of the present invention.
Figure 2:
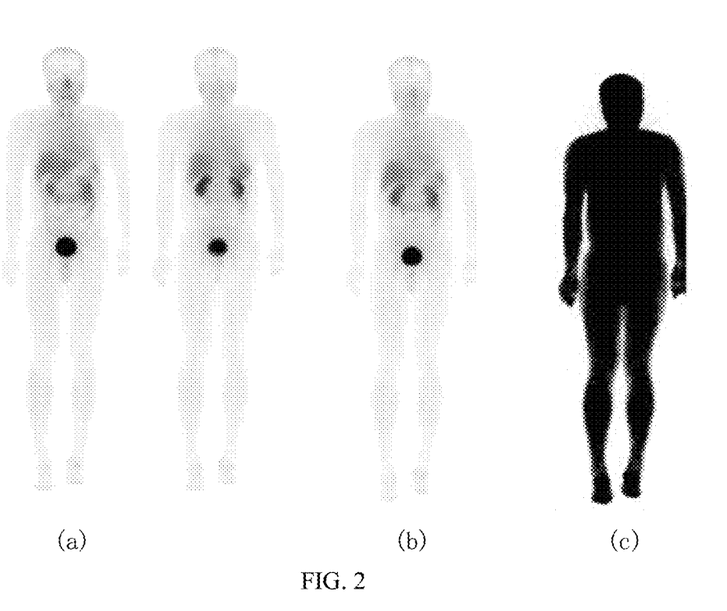
FIG. 2 is an example diagram of calculating an average image and segmenting all the radioactive uptake areas of human body by using anteroposterior systemic plain film images according to one embodiment of the present invention, among them.

As shown in FIG. 1, the method for calculating SUV normalization coefficient in a SPETOMOGRAPHIC quantitative tomographic image in this embodiment includes the following steps:

a) as shown in FIG. 2(a) and FIG. 2(b), averaging the anterior plain film image and posterior plain film image obtained by performing plain film scanning on a subject's whole body to get an average image, from which the area corresponding to the radioactive uptake site in the subject is segmented, and defined as an effective radioactive uptake area, b) correcting attenuation coefficient of human body, detection efficiency and acquisition time for each pixel value in the effective radioactive uptake area within said average image, and calculating the average radioactive uptake activity of the human body part corresponding to each pixel in the anteroposterior direction, further to figure out the quantitative two-dimensional radioactive uptake activity image after averaging each part of the human body corresponding to the average image in the anteroposterior direction, wherein said attenuation coefficient of human body is an average linear attenuation coefficient of the part of human body corresponding to a pixel value, c) averaging all the effective radioactive uptake area pointed at by said quantitative two-dimensional radioactive uptake activity image obtained in step b, and performing volume normalization and decay time correction to figure out the average radiopharmaceutical activity concentration absorbed in the subject, which is a SUV normalization coefficient used to calculate a SPETOMOGRAPHIC quantitative tomography image.

In the method for calculating SUV normalization coefficient in a SPETOMOGRAPHIC quantitative tomographic image, the average radiopharmaceutical activity concentration absorbed in the subject is quantitatively figured out by the SPETOMOGRAPHIC systemic image scanned in clinical routine practice as a coefficient for normalizing the pixel values of the quantitative three-dimensional tomographic images of the tomographic scan at the same or a similar time point, and then the SUV value of the region of interest in the SPETOMOGRAPHIC quantitative tomography image is further figured out. Compared with the existing calculation methods based on medicamentous injection dose and weight, there are two advantages.

In terms of accuracy, this method avoids errors in operating and recording the drug injection dose from affecting the accuracy of the SUV value calculation, and at the same time, it can correct and compensate for some special factors such as bladder uptake, radioactive contamination of body surface, at the level of plain film images according to clinical use habits and the actual situation of patients. For example, a predefined area of invalid radioactive uptake is segmented to improve the accuracy of the SUV normalization coefficient calculation, further enhance the accuracy of the SUV value calculation.

In terms of reliability, since all the input data of the algorithm of this method are derived from the Dicom image data and file header information output by the SPETOMOGRAPHIC device, it can be read and operated fully automatically, without the need for manual operation and keeping separate records, so it has higher reliability and better traceability.

Preferably, in step a, the average image is obtained by calculating a geometric average value or an arithmetic average value of pixel values of pixels corresponding to all spatial positions in said anterior plain film image and posterior plain film image.

The calculation process in detail is as follows:

The arithmetic average value is $P_i=(A_i+B_i)/2$, and the geometric average value is $P_i=\sqrt{A_i*B_i}$.

wherein, A is an anterior plain film image, B is a posterior plain film image, P is an average image, and i=1, 2, ..., I are all pixel index number of the anterior plain film image or all pixel index number of the posterior plain film image. Before calculating the average image, the anterior plain film image or the posterior plain film image is reversed or panned, in order to make the same pixel number correspond to the anterior and posterior projections of the same part of the human body, respectively.

Figure 3:
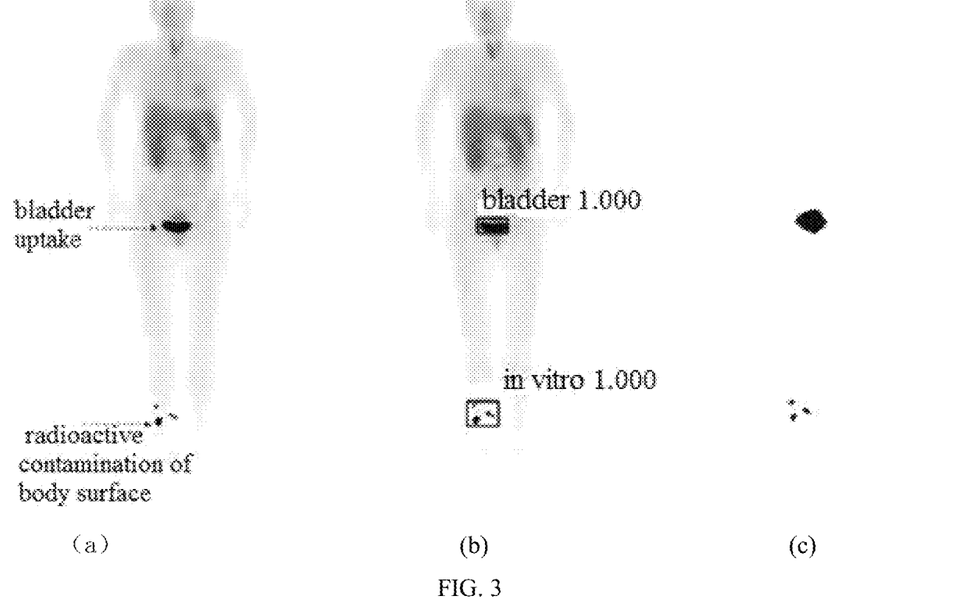
FIG. 3 is an example diagram of an area where inactive radioactive uptake such as bladder uptake and injection residue on the body surface is automatically detected in a SPETOMOGRAPHIC systemic plain scan image of one embodiment of the present invention, among them.

Preferably, the obtaining of the effective radioactive uptake area in step a specifically comprises:

first segmenting all areas corresponding to the radioactive uptake site of human body in said average image by an image segmentation method based on thresholds or texture features, then detecting a pre-defined invalid radioactive uptake area in said average image by a deep-learning or machine-learning algorithm, as shown in FIG. 3(b), next segmenting all the detected invalid radioactive uptake areas by a level set segmentation method or a deep-learning-based segmentation method, as shown in FIG. 3(c), and setting a pixel value corresponding to said invalid radioactive uptake area to 0 or an average value of surrounding areas in said average image, thereby obtaining the effective radioactive uptake region in said average image.

The obtained average image includes two parts, which respectively correspond to the foreground of the distribution of radiopharmaceuticals absorbed in human body and the backdrop of the corresponding background noise. Therefore, the existing image segmentation algorithms such as threshold, contour detection, watershed, region growing, or level set need, are applied to the average image to segment the foreground area where all the radiopharmaceuticals are absorbed corresponding to human body. That is, all the regions in the average image corresponding to the uptake of radioactivity in human body are segmented, as shown in FIG. 2(c).

In the foreground area where all the radiopharmaceuticals are absorbed corresponding to human body, as shown in FIG. 2(c), Some areas are invalid areas, that is, the areas that have no substantial meaning or affect the accuracy of the calculation for the average radioactivity concentration of human body, and divided by the pre-definition. The pre-defined invalid radioactive uptake area can be the parts of bladder uptake and radioactive contamination of body surface as shown in FIG. 3(a).

In the average image, the entire radioactive uptake area of the subject's human body is extracted by image segmentation, and a predefined invalid radioactive uptake area is further detected and segmented by applying the methods of machine learning and image segmentation, then the obtained invalid radioactive uptake area is excluded from all the radioactive uptake areas of the subject to obtain an effective radioactive uptake area in the average image. The algorithm of deep learning or machine learning either is existing algorithms.

Preferably, the obtaining of said quantitative two-dimensional radioactive uptake activity image in step b specifically comprises:

b1) correcting the attenuation coefficient of human body, wherein a SPETOMOGRAPHIC systemic plain film image and a local TOMOGRAPHIC tomographic image of a subject, and a three-dimensional attenuation coefficient chart based on digital human model are applied to jointly perform image registration, and then the average linear attenuation coefficient corresponding to all effective radioactive uptake areas in the subject is obtained, b2) correcting the detection efficiency, wherein types of the SPETOMOGRAPHIC acquisition device and collimator are read from a Dicom data file header information of said SPETOMOGRAPHIC systemic plain film image, and used them to calculate gamma photon detection efficiency, and then the pixel value of the SPETOMOGRAPHIC systemic plain film image is divided by the gamma photon detection efficiency, to figure out the number of gamma photons cumulatively emitted from corresponding parts of human body, b3) performing normalization correction of acquisition time, wherein acquisition time of the systemic plain film image and the SPETOMOGRAPHIC tomographic image from the Dicom data file header information of the subject's SPETOMOGRAPHIC systemic plain film image is read, then a normalization calculation is performed on the number of gamma photons obtained in step b2, and the quantitative two-dimensional radioactive uptake activity image is figured out after averaging the three-dimensional spatial distribution of the radioactive uptake activity of each part of the human body corresponding to said average image in the anteroposterior direction.

In the step b and the step c, the acquisition parameters such as the SPETOMOGRAPHIC acquisition device type, the collimator type, the image pixel size, the time interval between systemic plain film and tomography, and the equivalent scanning time of systemic plain film are automatically read from the Dicom data file header, to be used to perform the correction of detection sensitivity, acquisition time, radioactive decay and volume normalization on the image to accurately figure out the average radiopharmaceutical activity concentration absorbed in the subject.

In the step b3, a normalization correction of acquisition time is performed. The acquisition time (Unit: s) of the systemic plain film image and the SPETOMOGRAPHIC tomographic image from the Dicom data file header information of the subject's SPETOMOGRAPHIC systemic plain film image is read, then a normalization calculation is performed on the number of gamma photons obtained in step b2, and the quantitative two-dimensional radioactive uptake activity image (Unit: Bq) of each part of the human body corresponding to said average image in the anteroposterior direction (that is, the direction is perpendicular to the plane of the detector in the acquisition of the systemic plain film image) is figured out.

Figure 4:
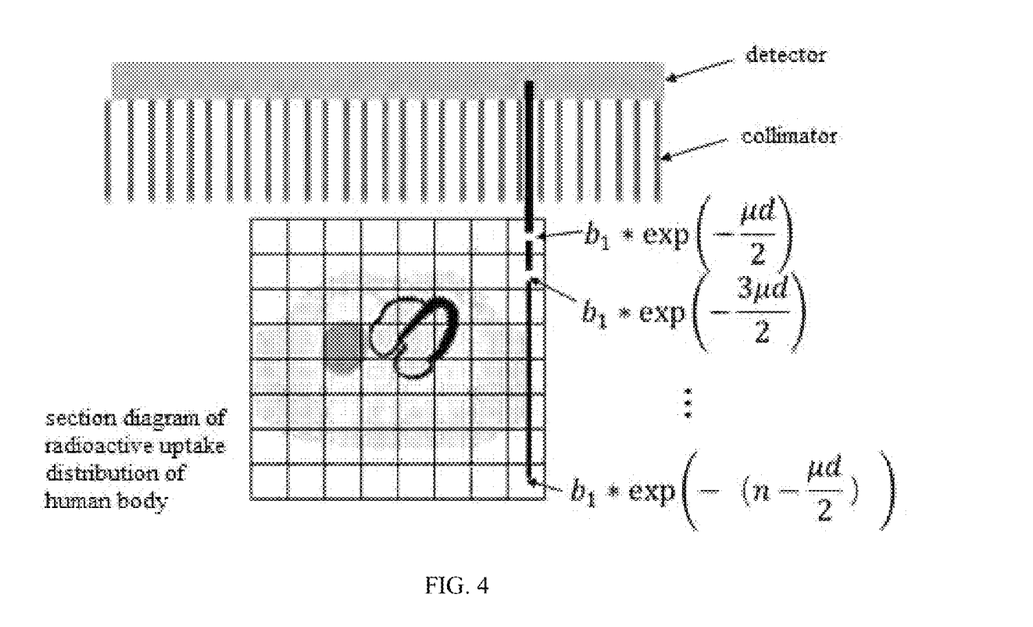
FIG. 4 is an example diagram of a mathematical model of SPETOMOGRAPHIC projection data acquisition based on the assumption that the radiopharmaceuticals and the attenuation coefficient of human body are evenly distributed in the anteroposterior direction in one embodiment of the present invention.

Preferably, in step b3, assuming that the radiopharmaceuticals and attenuation coefficients in different parts of human body are evenly distributed in the anteroposterior direction, as shown in FIG. 4, a mathematical model of SPETOMOGRAPHIC projection data acquisition is established in accordance with $$P_i = t * s_{col} * b_i * \exp\left(-\frac{\mu_i d}{2}\right) * \sum_{j=0}^{n_i-1} \exp(-\mu_i j d),$$

$$= t * s_{col} * b_i * \exp\left(-\frac{\mu_i d}{2}\right) \frac{1 - \exp(-\mu_i n_i d)}{1 - \exp(-\mu_i d)}$$

where $P_i$, $i \in I_0$ is the pixel value of all pixels included in the effective radioactive uptake area $I_0$ in said average image, and i is the pixel index number, and d is the side length of the graphic pixel of the SPETOMOGRAPHIC systemic plain film image, read from the Dicom data file header information of the SPETOMOGRAPHIC systemic plain film image, and $b_i$ is the average radioactive uptake activity of the radioactive uptake site of human body corresponding to the pixels i in said average image in the anteroposterior direction, and $s_{col}$ is the detector sensitivity, $s_{col}$ is obtained from the product parameter description table of the SPETOMOGRAPHIC acquisition device and collimator, and t is the equivalent acquisition time read from the Dicom data file header information of the SPETOMOGRAPHIC systemic plain film image, and $\mu_i$ is the average linear attenuation coefficient of the radioactive uptake site of human body corresponding to the pixel i in the average image in the anteroposterior direction, and $n_i$ is the voxel number obtained by one-dimensional discretization of the radioactive uptake site of human body corresponding to the pixel i in the average image in the anteroposterior direction with the side length d as the sampling size, that is what the thickness of the radioactive uptake site of human body in the anteroposterior direction is divided by the side length d to figure out.

Because the differential distribution of the radioactive uptake and attenuation coefficient in the human body has little affect on the final average result, It can be assumed that the radiopharmaceuticals and attenuation coefficients in different parts of human body are evenly distributed in the anteroposterior direction. The physical process of converting the three-dimensional radiopharmaceutical distribution in human body into the plain film projection data can be approximated as the sum of proportional series, to be convenient for accurately figuring out the average radiopharmaceutical activity concentration.

d is the side length of the graphic pixel of the SPETOMOGRAPHIC systemic plain film image. It is read from the Dicom data file header information of the SPETOMOGRAPHIC systemic plain film image. Here, the voxels with d as side length are used to discretize the radiopharmaceutical 3D distribution of human body. $b_i$ is the average radioactive uptake activity of the radioactive uptake site of human body corresponding to the pixels i in the average image in the anteroposterior direction, that is, the radioactivity uptake value in the unit voxel that is obtained by averaging the radioactive uptake site of human body corresponding to the pixels i in the average image in the anteroposterior direction. $s_{col}$ is the sensitivity of the detector, which is defined as the probability that the number of gamma photons emitted from a point in human body is detected by the detector after being collimated by the collimator (regardless of the attenuation scattering effect). The value $s_{col}$ is related to the type of the SPETOMOGRAPHIC acquisition device and the collimator. The information of the type of the SPETOMOGRAPHIC acquisition device and the collimator can be obtained from the Dicom data file header information, and the value $s_{col}$ can be further found out through the product parameter description table provided by the manufacturer. Figuring out the estimated values of $\mu_i$ and $n_i$ is a prerequisite for solving $b_i$ from the mathematical model of SPETOMOGRAPHIC projection data acquisition.

Preferably, in step b3, the estimated value of $\mu_i$ and $n_i$ in said mathematical model of SPETOMOGRAPHIC projection data acquisition is obtained by step b1, specifically comprising:

for the part of human body with the local TOMOGRAPHIC tomographic image, converting the local TOMOGRAPHIC tomographic image of the part of human body into the attenuation coefficient chart corresponding to 140 keV gamma photons for the SPETOMOGRAPHIC imaging by bilinear transformation, then figuring out the average linear attenuation coefficient $\mu_i$, voxel number $n_i$, and anteroposterior cumulative attenuation coefficient exp $(-\mu_i n_i d)$ of the effective radioactive uptake area covered by and according to said attenuation coefficient chart, for the part of human body lacking the local TOMOGRAPHIC tomographic image, performing image registration on the SPETOMOGRAPHIC systemic plain film image and the three-dimensional attenuation coefficient chart based on digital human model to obtain a plain film chart of anteroposterior cumulative attenuation coefficient, that is $\exp(-\mu_i n_i d)$, $i \in I_0$.

then as shown in FIG. 6(a) to FIG. 6(j), performing 3D registration on the local TOMOGRAPHIC tomographic image of the subject and the three-dimensional attenuation coefficient chart based on digital human model to obtain the anatomical part that best matches the local TOMOGRAPHIC tomographic image of the subject, thereby obtaining an anteroposterior thickness proportionality factor of the mathematical model of the SPETOMOGRAPHIC projection data acquisition to the corresponding parts of the subject, then applying the anteroposterior thickness proportionality factor to the anatomical part that is not covered by the local TOMOGRAPHIC tomographic image of the subject in the three-dimensional digital human model, thereby obtaining an estimated thickness value of each part of the subject's whole body, that is, $n_i d$, $i \in I_0$, thus, figuring out the average linear attenuation coefficient $\mu_i$ of all effective radioactive uptake areas, in said step b3, according to the mathematical model of the SPETOMOGRAPHIC projection data acquisition, obtaining the average radioactive uptake activity $b_i$ of the radioactive uptake site of human body corresponding to the pixels i in the average image in the anteroposterior direction, in accordance with $$b_i = P_i * \exp\left(\frac{\mu_i d}{2}\right) \frac{1 - \exp(-\mu_i d)}{(1 - \exp(-\mu_i n_i d)) * t * s_{col}}.$$

This method is applied to the systemic plain film and combined with the quantitative tomography data of local SPETOMOGRAPHIC/TOMOGRAPHIC, in this situation, firstly for the part of human body with the local TOMOGRAPHIC tomographic image, the local TOMOGRAPHIC tomographic image of the part of human body can be converted into the attenuation coefficient chart corresponding to 140 keV gamma photons for the SPETOMOGRAPHIC imaging by bilinear transformation, then the average linear attenuation coefficient $\mu_i$, voxel number $n_i$, and anteroposterior cumulative attenuation coefficient exp $(-\mu_i n_i d)$ of the effective radioactive uptake area covered by said attenuation coefficient chart are figured out according to said attenuation coefficient chart.

Figure 5:
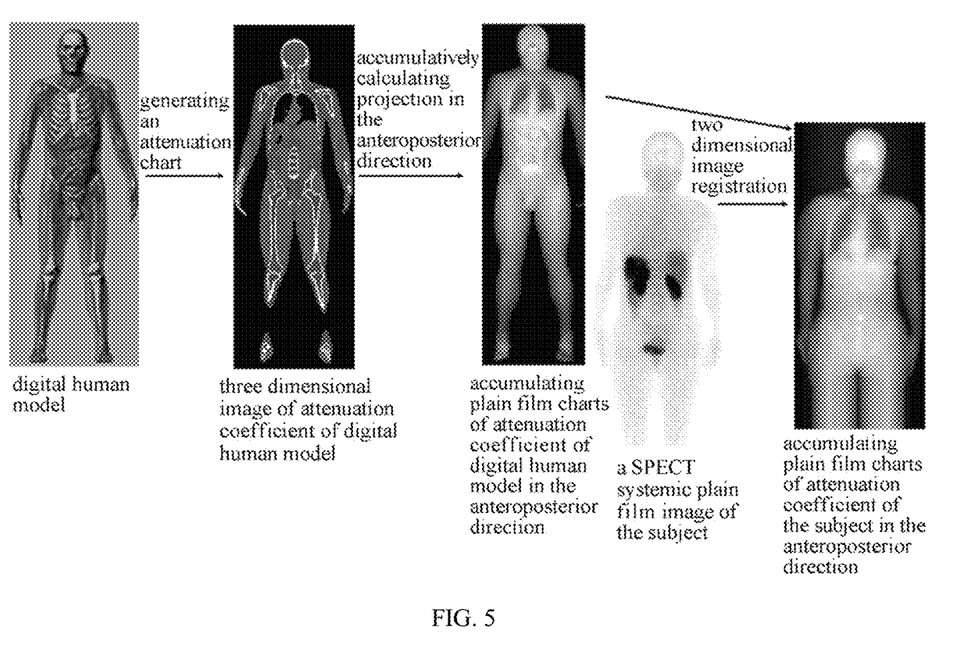
FIG. 5 is an exemplary flowchart of a method for generating a plain film chart of anteroposterior cumulative attenuation coefficient corresponding to all effective radioactive uptake areas of human body according to one embodiment of the present invention.
Figure 6:
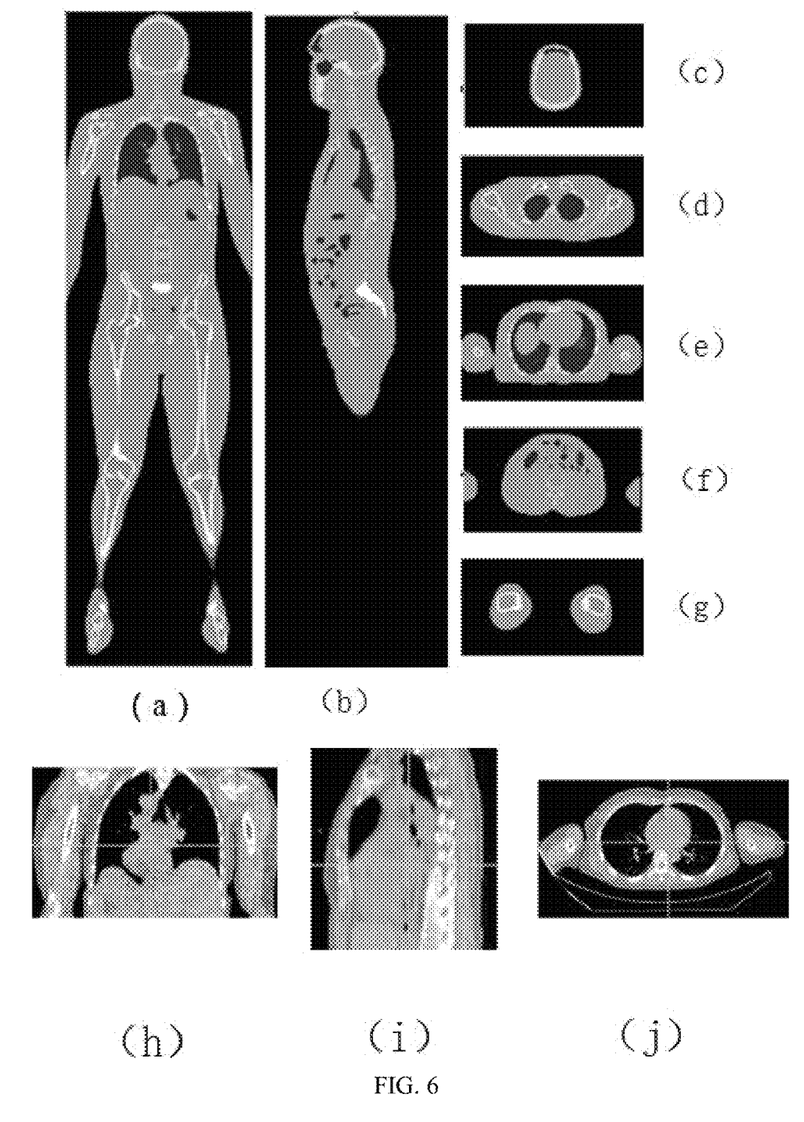
FIG. 6 is an example diagram of a method for estimating the average linear attenuation coefficient and thickness dimension of each part of human body in the anteroposterior direction according to an embodiment of the present invention, among them.

For the part of human body lacking the local TOMOGRAPHIC tomographic image as shown in FIG. 5, Firstly, a digital human model (such as XCAT phantom, etc.) commonly used in the field of nuclear medicine and radiotherapy is adopted to generate a systemic three-dimensional attenuation coefficient chart of the digital human, then the three-dimensional attenuation coefficient chart based on the digital human model is projected in the anteroposterior directions to obtain a plain film chart of cumulative attenuation coefficient based on the digital human model. Image registration is performed on the plain film chart of cumulative attenuation coefficient and the subject's SPETOMOGRAPHIC systemic plain film image, to obtain a plain film chart of anteroposterior cumulative attenuation coefficient of the subject, that is $\exp(-\mu_i n_i d)$, $i \in I_0$.

Further, 3D registration is performed on the local TOMOGRAPHIC tomographic image of the subject and the three-dimensional attenuation coefficient chart based on digital human model, firstly to obtain the anatomical part that best matches the local TOMOGRAPHIC tomographic image of the subject, thereby obtain an anteroposterior thickness proportionality factor of the mathematical model of the SPETOMOGRAPHIC projection data acquisition to the corresponding parts of the subject, then the anteroposterior thickness proportionality factor is applied to the anatomical part that is not covered by the local TOMOGRAPHIC tomographic image of subject in the three-dimensional digital human model, to obtain an estimated thickness value of each part of the subject's whole body, that is, $n_i d$, $i \in I_0$, based on $\exp(\mu_i n_i d)$ and $n_i d$ that are obtained in the above method, thus the average linear attenuation coefficient $\mu_i$ of all effective radioactive uptake areas is figured out. Therefore, $b_i$ can be derived from the mathematical model of SPETOMOGRAPHIC projection data acquisition.

Preferably, said step c specifically comprises:

c1) averaging all the effective radioactive uptake area pointed at by said quantitative two-dimensional radioactive uptake activity image obtained in step b, and performing volume normalization by using the pixel size contained in the Dicom data file header information of the SPETOMOGRAPHIC systemic plain film image to obtain the average radioactivity concentration in human body in the intermediate instant of the acquisition of the SPETOMOGRAPHIC systemic plain film image.

c2) performing decay time correction according to the acquisition time interval in the SPETOMOGRAPHIC tomographic image data of the subject and the Dicom data file header information of the SPETOMOGRAPHIC systemic plain film image to figure out the average radiopharmaceutical activity concentration absorbed in the subject in accordance with $$b = \frac{\Sigma_{i \in I_0} b_i n_i}{\Sigma_{i \in I_0} n_i} \frac{\exp[-\lambda(t_2 - t_1)]}{d^2},$$

where $t_1$ is the intermediate instant of the acquisition of the SPETOMOGRAPHIC systemic plain film image, $t_2$ is the intermediate instant of the acquisition of the SPETOMOGRAPHIC tomographic image, and $\lambda$ is the radionuclide decay coefficient, c3) obtaining the average radiopharmaceutical activity concentration b that is normalization coefficient used to calculate the standard uptake value of the SPETOMO- GRAPHIC quantitative tomographic image, and using said average radiopharmaceutical activity concentration for the normalization of the SPETOMOGRAPHIC quantitative tomography physical image to obtain the SPETOMOGRAPHIC quantitative tomographic image with the SUV value as the dimension, and calculating and evaluating the SUV value of any region of interest in said SPETOMOGRAPHIC quantitative tomographic image.

In step c the average value of the one-dimensional average radioactivity activity image obtained in step b pointing at all effective ingestion parts of the human body (obtained in step a) is calculated, and the pixel size contained in the Dicom data file header information of the SPETOMOGRAPHIC systemic plain film image is used to perform volume normalization to obtain the average radioactivity concentration in human body in the intermediate instant of the acquisition of the SPETOMOGRAPHIC systemic plain film image.

Radioactive decay correction is further performed according to the acquisition time interval in the SPETOMOGRAPHIC tomographic image data and the Dicom data file header information of the SPETOMOGRAPHIC systemic plain film image to obtain the average radiopharmaceutical activity concentration in human body in the intermediate instant of the tomographic acquisition (Unit: Bq/ml), that is, the normalization coefficient of the uptake value of the quantitative tomographic image is calculated and used for the normalization of the SPETOMOGRAPHIC quantitative tomography physical image (Unit of pixel value: Bq/ml), so then a SPETOMOGRAPHIC quantitative tomographic images of with the SUV value as dimension can be obtained, further to calculate and evaluate the SUV value of any region of interest.

Embodiment 2

The system for calculating SUV normalization coefficient in a SPETOMOGRAPHIC quantitative tomographic image in this embodiment includes:

a module for calculating an effective radioactive uptake area, as shown in FIG. 2(a) and FIG. 2(b), which is used to average the anterior plain film image and posterior plain film image obtained by performing plain film scanning on a subject's whole body to get an average image, from which the area corresponding to the radioactive uptake site in the subject is segmented, and defined as an effective radioactive uptake area, a module for calculating a quantitative two-dimensional radioactive uptake activity image, which is used to correct attenuation coefficient of human body, detection efficiency and acquisition time for each pixel value in the effective radioactive uptake area within said average image, and calculate the average radioactive uptake activity of the human body part corresponding to each pixel in the anteroposterior direction, further to figure out the quantitative two-dimensional radioactive uptake activity image after averaging each part of the human body corresponding to the average image in the anteroposterior direction, wherein said attenuation coefficient of human body is an average linear attenuation coefficient of the part of human body corresponding to a pixel value, and a module for calculating an average radiopharmaceutical activity concentration, which is used to average all the effective radioactive uptake area pointed at by said quantitative two-dimensional radioactive uptake activity image, and perform volume normalization and decay time correction to figure out the average radiopharmaceutical activity concentration absorbed in the subject, which is a SUV normalization coefficient used to calculate a SPETOMOGRAPHIC quantitative tomography image.

In the system for calculating SUV normalization coefficient in a SPETOMOGRAPHIC quantitative tomographic image, the average radiopharmaceutical activity concentration absorbed in the subject is quantitatively figured out by the SPETOMOGRAPHIC systemic image scanned in clinical routine practice as a coefficient for normalizing the pixel values of the quantitative three-dimensional tomographic images of the tomographic scan at the same or a similar time point, and then the SUV value of the region of interest in the SPETOMOGRAPHIC quantitative tomography image is further figured out. Compared with the existing calculation methods based on medicamentous injection dose and weight, there are two advantages.

In terms of accuracy, this system avoids errors in operating and recording the drug injection dose from affecting the accuracy of the SUV value calculation, and at the same time, it can correct and compensate for some special factors such as bladder uptake, radioactive contamination of body surface, at the level of plain film images according to clinical use habits and the actual situation of patients. For example, a predefined area of invalid radioactive uptake is segmented to improve the accuracy of the SUV normalization coefficient calculation, further enhance the accuracy of the SUV value calculation.

In terms of reliability, since all the input data of the algorithm of this system are derived from the Dicom image data and file header information output by the SPETOMOGRAPHIC device, it can be read and operated fully automatically, without the need for manual operation and keeping separate records, so it has higher reliability and better traceability.

Preferably, said module for calculating an effective radioactive uptake area comprises:

a first submodule, which is used to segment all areas corresponding to the radioactive uptake site of human body in said average image by an image segmentation method based on thresholds or texture features, a second submodule, which is used to detect a pre-defined invalid radioactive uptake area in said average image by a deep-learning or machine-learning algorithm, as shown in FIG. 3(b), and a third submodule, which is used to segment all the detected invalid radioactive uptake areas by a level set segmentation method or a deep-learning-based segmentation method, as shown in FIG. 3(c), and set a pixel value corresponding to said invalid radioactive uptake area to 0 or an average value of surrounding areas in said average image, thereby obtain the effective radioactive uptake region in said average image.

The average image is obtained by calculating a geometric average value or an arithmetic average value of pixel values of pixels corresponding to all spatial positions in said anterior plain film image and posterior plain film image.

The calculation process in detail is as follows:

The arithmetic average value is $P_i=(A_i+B_i)/2$, and the geometric average value is $P_i=\sqrt{A_i*B_i}$.

wherein, A is an anterior plain film image, B is a posterior plain film image, P is an average image, and i=1, 2, . . . , I are all pixel index number of the anterior plain film image or all pixel index number of the posterior plain film image. Before calculating the average image, the anterior plain film image or the posterior plain film image is reversed or panned, in order to make the same pixel number correspond to the anterior and posterior projections of the same part of the human body, respectively.

Preferably, said module for calculating a quantitative two-dimensional radioactive uptake activity image comprises:

a fourth submodule for correcting the attenuation coefficient of human body, wherein a SPETOMOGRAPHIC systemic plain film image and a local TOMOGRAPHIC tomographic image of a subject, and a three-dimensional attenuation coefficient chart based on digital human model are applied to jointly perform image registration, and then the average linear attenuation coefficient corresponding to all effective radioactive uptake areas in the subject is obtained, a fifth submodule for correcting the detection efficiency, wherein types of the SPETOMOGRAPHIC acquisition device and collimator are read from a Dicom data file header information of said SPETOMOGRAPHIC systemic plain film image, and used them to calculate gamma photon detection efficiency, and then the pixel value of the SPETOMOGRAPHIC systemic plain film image is divided by the gamma photon detection efficiency, to figure out the number of gamma photons cumulatively emitted from corresponding parts of human body, and a sixth submodule for performing normalization correction of acquisition time, wherein acquisition time of the systemic plain film image and the SPETOMOGRAPHIC tomographic image from the Dicom data file header information of the subject's SPETOMOGRAPHIC systemic plain film image is read, then a normalization calculation is performed on the number of gamma photons obtained, and the quantitative two-dimensional radioactive uptake activity image is figured out after averaging the three-dimensional spatial distribution of the radioactive uptake activity of each part of the human body corresponding to said average image in the anteroposterior direction.

The acquisition parameters such as the SPETOMOGRAPHIC acquisition device type, the collimator type, the image pixel size, the time interval between systemic plain film and tomography, and the equivalent scanning time of systemic plain film are automatically read from the Dicom data file header, to be used to perform the correction of detection sensitivity, acquisition time, radioactive decay and volume normalization on the image to accurately figure out the average radiopharmaceutical activity concentration absorbed in the subject.

Preferably, said sixth submodule is used to assume that the radiopharmaceuticals and attenuation coefficients in different parts of human body are evenly distributed in the anteroposterior direction, a mathematical model of SPETOMOGRAPHIC projection data acquisition is established in accordance with $$P_i = t * s_{col} * b_i * \exp\left(-\frac{\mu_i d}{2}\right) * \sum_{j=0}^{n_i-1} \exp(-\mu_i j d),$$

$$= t * s_{col} * b_i * \exp\left(-\frac{\mu_i d}{2}\right) \frac{1 - \exp(-\mu_i n_i d)}{1 - \exp(-\mu_i d)}$$

where $P_i$, $i \in I_0$ is the pixel value of all pixels included in the effective radioactive uptake area $I_0$ in said average image, and i is the pixel index number, and d is the side length of the graphic pixel of the SPETOMOGRAPHIC systemic plain film image, read from the Dicom data file header information of the SPETOMOGRAPHIC systemic plain film image, and $b_i$ is the average radioactive uptake activity of the radioactive uptake site of human body corresponding to the pixels i in said average image in the anteroposterior direction, and $s_{col}$ is the detector sensitivity, $s_{col}$ is obtained from the product parameter description table of the SPETOMOGRAPHIC acquisition device and collimator, and t is the equivalent acquisition time read from the Dicom data file header information of the SPETOMOGRAPHIC systemic plain film image, and $\mu_i$ is the average linear attenuation coefficient of the radioactive uptake site of human body corresponding to the pixel i in the average image in the anteroposterior direction, and $n_i$ is the voxel number obtained by one-dimensional discretization of the radioactive uptake site of human body corresponding to the pixel i in the average image in the anteroposterior direction with the side length d as the sampling size, that is what the thickness of the radioactive uptake site of human body in the anteroposterior direction is divided by the side length d to figure out.

Because the differential distribution of the radioactive uptake and attenuation coefficient in the human body has little affect on the final average result, It can be assumed that the radiopharmaceuticals and attenuation coefficients in different parts of human body are evenly distributed in the anteroposterior direction. The physical process of converting the three-dimensional radiopharmaceutical distribution in human body into the plain film projection data can be approximated as the sum of proportional series, to be convenient for accurately figuring out the average radiopharmaceutical activity concentration.

Preferably, the estimated value of $\mu_i$ and $n_i$ in said in said fifth submodule is obtained by said fourth submodule, and said fourth submodule specifically comprises:

for the part of human body with the local TOMOGRAPHIC tomographic image, converting the local TOMOGRAPHIC tomographic image of the part of human body into the attenuation coefficient chart corresponding to 140 keV gamma photons for the SPETOMOGRAPHIC imaging by bilinear transformation, then figuring out the average linear attenuation coefficient $\mu_i$, voxel number $n_i$, and anteroposterior cumulative attenuation coefficient $\exp(-\mu_i n_i d)$ of the effective radioactive uptake area covered by and according to said attenuation coefficient chart, for the part of human body lacking the local TOMOGRAPHIC tomographic image, performing image registration on the SPETOMOGRAPHIC systemic plain film image and the three-dimensional attenuation coefficient chart based on digital human model to obtain a plain film chart of anteroposterior cumulative attenuation coefficient, that is $\exp(-\mu_i n_i d)$, $i \in I_0$, then performing 3D registration on the local TOMOGRAPHIC tomographic image of the subject and the three-dimensional attenuation coefficient chart based on digital human model to obtain the anatomical part that best matches the local TOMOGRAPHIC tomographic image of the subject, thereby obtaining an anteroposterior thickness proportionality factor of the mathematical model of the SPETOMOGRAPHIC projection data acquisition to the corresponding parts of the subject, then applying the anteroposterior thickness proportionality factor to the anatomical part that is not covered by the local TOMOGRAPHIC tomographic image of the subject in the three-dimensional digital human model, thereby obtaining an estimated thickness value of each part of the subject's whole body, that is, $n_i d$, $i \in I_0$, thus, figuring out the average linear attenuation coefficient $\mu_i$ of all effective radioactive uptake areas, In said fifth submodule, according to the mathematical model of the SPETOMOGRAPHIC projection data acquisition, obtaining the average radioactive uptake activity $b_i$ of the radioactive uptake site of human body corresponding to the pixels i in the average image in the anteroposterior direction in accordance with $$b_i = P_i * \exp\left(\frac{\mu_i d}{2}\right) \frac{1 - \exp(-\mu_i d)}{(1 - \exp(-\mu_i n_i d)) * t * s_{col}}.$$

Preferably, said module for calculating an average radiopharmaceutical activity concentration comprises:

a seventh submodule which is used to average all the effective radioactive uptake area pointed at by said quantitative two-dimensional radioactive uptake activity image, and performs volume normalization by using the pixel size contained in the Dicom data file header information of the SPETOMOGRAPHIC systemic plain film image to obtain the average radioactivity concentration in human body in the intermediate instant of the acquisition of the SPETOMOGRAPHIC systemic plain film image.

an eighth submodule which is used to perform decay time correction according to the acquisition time interval in the SPETOMOGRAPHIC tomographic image data of the subject and the Dicom data file header information of the SPETOMOGRAPHIC systemic plain film image to figure out the average radiopharmaceutical activity concentration absorbed in the subject in accordance with $$b = \frac{\Sigma_{i \in I_0} b_i n_i}{\Sigma_{i \in I_0} n_i} \frac{\exp[-\lambda(t_2 - t_1)]}{d^2},$$

where $t_1$ is the intermediate instant of the acquisition of the SPETOMOGRAPHIC systemic plain film image, $t_2$ is the intermediate instant of the acquisition of the SPETOMOGRAPHIC tomographic image, ands is the radionuclide decay coefficient, and a ninth submodule which is used to obtain the average radiopharmaceutical activity concentration b used to perform normalization on the SPETOMOGRAPHIC quantitative tomographic image, wherein the SPETOMOGRAPHIC quantitative tomographic image with the SUV value as the dimension can be obtained, and the SUV value of any region of interest in said SPETOMOGRAPHIC quantitative tomographic image is calculated and evaluated.

Embodiment 3

Figure 7:
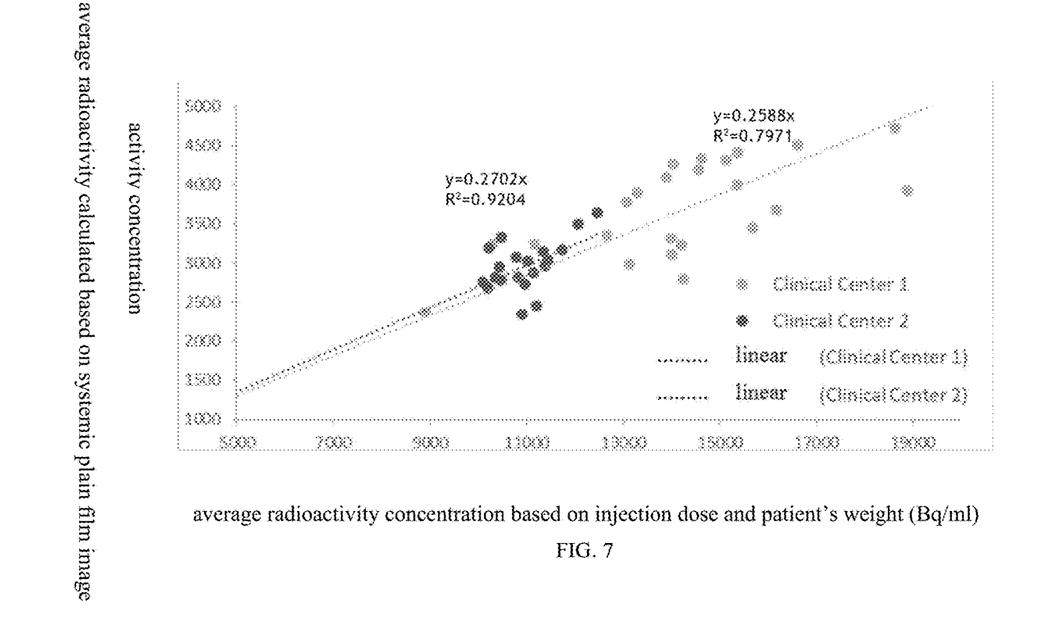
FIG. 7 is an example diagram for verifying correlation results between the average radiopharmaceutical activity concentration absorbed in a subject calculated in this method and the traditional method in one embodiment of the present invention.

This example applies the method described in Example 1 to two groups of clinical trial subjects where $^{99m}$Tc-3PRGD2 is used for SPETOMOGRAPHIC imaging. The two groups of subjects come from different medical centers, the clinical center1 and the clinical center2, of which the subjects from the clinical center1 are the group of the patients who are clinically diagnosed with breast cancer, and the subjects from the clinical center2 are the group of the healthy volunteers. The SPETOMOGRAPHIC systemic plain film and the local SPETOMOGRAPHIC tomographic imaging of at least one site are performed on both groups of subjects, and the injection dose, injection time and subject weight are recorded before imaging. The correlation analysis is performed on the average radiopharmaceutical activity concentration absorbed in the subject which is figured out by using the method described in Embodiment 1, and the average concentration which is figured out by using the method that the injection dose divides the body weight, as shown in FIG. 7, Both groups of subjects obtain a good correlation, and the correlation coefficients were very close, so it proves that the method described in Example 1 is effective.

The technical principles of the present invention have been described above with reference to specific embodiments. These descriptions are only for explaining the principle of the present invention, and cannot be interpreted in any way as a limit to the scope of protection of the present invention. Based on the descriptions herein, those skilled in the art can think of other specific embodiments of the present invention without creative work required, and these embodiments will fall into the protection scope of the present invention.

What is claimed is:

1. A method for calculating SUV normalization coefficient in a SPETOMOGRAPHIC quantitative tomographic image, wherein the method comprises the following steps:
    a) averaging the anterior plain film image and posterior plain film image obtained by performing plain film scanning on a subject's whole body to get an average image, from which the area corresponding to the radioactive uptake site in the subject is segmented, and defined as an effective radioactive uptake area,
    b) correcting attenuation coefficient of human body, detection efficiency and acquisition time for each pixel value in the effective radioactive uptake area within said average image, and calculating the average radioactive uptake activity of the human body part corresponding to each pixel in the anteroposterior direction, further to figure out the quantitative two-dimensional radioactive uptake activity image after averaging each part of the human body corresponding to the average image in the anteroposterior direction, wherein said attenuation coefficient of human body is an average linear attenuation coefficient of the part of human body corresponding to a pixel value,
    c) averaging all the effective radioactive uptake area pointed at by said quantitative two-dimensional radioactive uptake activity image obtained in step b, and performing volume normalization and decay time correction to figure out the average radiopharmaceutical activity concentration absorbed in the subject, which is a SUV normalization coefficient used to calculate a SPETOMOGRAPHIC quantitative tomography image.

2. The method according to claim 1, wherein in step a the average image is obtained by calculating a geometric average value or an arithmetic average value of pixel values of pixels corresponding to all spatial positions in said anterior plain film image and posterior plain film image.

3. The method according to claim 1, wherein the obtaining of the effective radioactive uptake area in step a specifically comprises:
    first segmenting all areas corresponding to the radioactive uptake site of human body in said average image by an image segmentation method based on thresholds or texture features,
    then detecting a pre-defined invalid radioactive uptake area in said average image by a deep-learning or machine-learning algorithm,
    next segmenting all the detected invalid radioactive uptake areas by a level set segmentation method or a deep-learning-based segmentation method, and setting a pixel value corresponding to said invalid radioactive uptake area to 0 or an average value of surrounding areas in said average image, thereby obtaining the effective radioactive uptake region in said average image.

4. The method according to claim 1, wherein the obtaining of said quantitative two-dimensional radioactive uptake activity image in step b specifically comprises the following steps:

b1) correcting the attenuation coefficient of human body, wherein a SPETOMOGRAPHIC systemic plain film image and a local TOMOGRAPHIC tomographic image of a subject, and a three-dimensional attenuation coefficient chart based on digital human model are applied to jointly perform image registration, and then the average linear attenuation coefficient corresponding to all effective radioactive uptake areas in the subject is obtained, b2) correcting the detection efficiency, wherein types of the SPETOMOGRAPHIC acquisition device and collimator are read from a Dicom data file header information of said SPETOMOGRAPHIC systemic plain film image, and used them to calculate gamma photon detection efficiency, and then the pixel value of the SPETOMOGRAPHIC systemic plain film image is divided by the gamma photon detection efficiency, to figure out the number of gamma photons cumulatively emitted from corresponding parts of human body, b3) performing normalization correction of acquisition time, wherein acquisition time of the systemic plain film image and the SPETOMOGRAPHIC tomographic image from the Dicom data file header information of the subject's SPETOMOGRAPHIC systemic plain film image is read, then a normalization calculation is performed on the number of gamma photons obtained in step b2, and the quantitative two-dimensional radioactive uptake activity image is figured out after averaging the three-dimensional spatial distribution of the radioactive uptake activity of each part of the human body corresponding to said average image in the anteroposterior direction.

5. The method according to claim 4, wherein in step b3 assuming that the radiopharmaceuticals and attenuation coefficients in different parts of human body are evenly distributed in the anteroposterior direction, a mathematical model of SPETOMOGRAPHIC projection data acquisition is established in accordance with $$P_i = t * s_{col} * b_i * \exp\left(-\frac{\mu_i d}{2}\right) * \sum_{j=0}^{n_i-1} \exp(-\mu_i j d),$$

$$= t * s_{col} * b_i * \exp\left(-\frac{\mu_i d}{2}\right) \frac{1 - \exp(-\mu_i n_i d)}{1 - \exp(-\mu_i d)}$$

where $P_i$, $i \in I_0$ is the pixel value of all pixels included in the effective radioactive uptake area $I_0$ in said average image, and i is the pixel index number, and d is the side length of the graphic pixel of the SPETOMOGRAPHIC systemic plain film image, read from the Dicom data file header information of the SPETOMOGRAPHIC systemic plain film image, and $b_i$ is the average radioactive uptake activity of the radioactive uptake site of human body corresponding to the pixels i in said average image in the anteroposterior direction, and $s_{col}$ is the detector sensitivity, $s_{col}$ is obtained from the product parameter description table of the SPETOMOGRAPHIC acquisition device and collimator, and t is the equivalent acquisition time read from the Dicom data file header information of the SPETOMOGRAPHIC systemic plain film image, and $\mu_i$ is the average linear attenuation coefficient of the radioactive uptake site of human body corresponding to the pixel i in the average image in the anteroposterior direction, and $n_i$ is the voxel number obtained by one-dimensional discretization of the radioactive uptake site of human body corresponding to the pixel i in the average image in the anteroposterior direction with the side length d as the sampling size, that is, the thickness of the radioactive uptake site of human body in the anteroposterior direction is divided by the side length d to figure out.

6. The method according to claim 5, wherein in step b3 the estimated value of and in said mathematical model of SPETOMOGRAPHIC projection data acquisition is obtained by step b1, specifically comprising:

for the part of human body with the local TOMOGRAPHIC tomographic image, converting the local TOMOGRAPHIC tomographic image of the part of human body into the attenuation coefficient chart corresponding to 140 keV gamma photons for the SPETOMOGRAPHIC imaging by bilinear transformation, then figuring out the average linear attenuation coefficient $\mu_i$, voxel number $n_i$, and anteroposterior cumulative attenuation coefficient $\exp(-\mu_i n_i d)$ of the effective radioactive uptake area covered by and according to said attenuation coefficient chart, for the part of human body lacking the local TOMOGRAPHIC tomographic image, performing image registration on the SPETOMOGRAPHIC systemic plain film image and the three-dimensional attenuation coefficient chart based on digital human model to obtain a plain film chart of anteroposterior cumulative attenuation coefficient, that is $\exp(-\mu_i n_i d)$, $i \in I_0$, then performing 3D registration on the local TOMOGRAPHIC tomographic image of the subject and the three-dimensional attenuation coefficient chart based on digital human model to obtain the anatomical part that best matches the local TOMOGRAPHIC tomographic image of the subject, thereby obtaining an anteroposterior thickness proportionality factor of the mathematical model of the SPETOMOGRAPHIC projection data acquisition to the corresponding parts of the subject, then applying the anteroposterior thickness proportionality factor to the anatomical part that is not covered by the local TOMOGRAPHIC tomographic image of the subject in the three-dimensional digital human model, thereby obtaining an estimated thickness value of each part of the subject's whole body, that is, $n_i d$, $i \in I_0$, thus, figuring out the average linear attenuation coefficient $\mu_i$ of all effective radioactive uptake areas, in said step b3 according to the mathematical model of the SPETOMOGRAPHIC projection data acquisition, obtaining the average radioactive uptake activity $b_i$ of the radioactive uptake site of human body corresponding to the pixels i in the average image in the anteroposterior direction, in accordance with $$b_i = P_i * \exp\left(\frac{\mu_i d}{2}\right) \frac{1 - \exp(-\mu_i d)}{(1 - \exp(-\mu_i n_i d)) * t * s_{col}}.$$

7. The method according to claim 5, wherein said step c specifically comprises the following steps:

c1) averaging all the effective radioactive uptake area pointed at by said quantitative two-dimensional radioactive uptake activity image obtained in step b, and performing volume normalization by using the pixel size contained in the Dicom data file header information of the SPETOMOGRAPHIC systemic plain film image to obtain the average radioactivity concentration in human body in the intermediate instant of the acquisition of the SPETOMOGRAPHIC systemic plain film image.

c2) performing decay time correction according to the acquisition time interval in the SPETOMOGRAPHIC tomographic image data of the subject and the Dicom data file header information of the SPETOMOGRAPHIC systemic plain film image to figure out the average radiopharmaceutical activity concentration absorbed in the subject in accordance with $$b = \frac{\Sigma_{i \in I_0} b_i n_i}{\Sigma_{i \in I_0} n_i} \frac{\exp[-\lambda(t_2 - t_1)]}{d^2}$$

where $t_1$ is the intermediate instant of the acquisition of the SPETOMOGRAPHIC systemic plain film image, $t_2$ is the intermediate instant of the acquisition of the SPETOMOGRAPHIC tomographic image, and $\lambda$ is the radionuclide decay coefficient, c3) obtaining the average radiopharmaceutical activity concentration b that is normalization coefficient used to calculate the standard uptake value of the SPETOMOGRAPHIC quantitative tomographic image, and using said average radiopharmaceutical activity concentration b for the normalization of the SPETOMOGRAPHIC quantitative tomography physical image to obtain the SPETOMOGRAPHIC quantitative tomographic image with the SUV value as the dimension, and calculating and evaluating the SUV value of any region of interest in said SPETOMOGRAPHIC quantitative tomographic image.

8. A system for calculating SUV normalization coefficient in a SPETOMOGRAPHIC quantitative tomographic image, comprising:

a module for calculating an effective radioactive uptake area, which is used to average the anterior plain film image and posterior plain film image obtained by performing plain film scanning on a subject's whole body to get an average image, from which the area corresponding to the radioactive uptake site in the subject is segmented, and defined as an effective radioactive uptake area, a module for calculating a quantitative two-dimensional radioactive uptake activity image, which is used to correct attenuation coefficient of human body, detection efficiency and acquisition time for each pixel value in the effective radioactive uptake area within said average image, and calculate the average radioactive uptake activity of the human body part corresponding to each pixel in the anteroposterior direction, further to figure out the quantitative two-dimensional radioactive uptake activity image after averaging each part of the human body corresponding to the average image in the anteroposterior direction, wherein said attenuation coefficient of human body is an average linear attenuation coefficient of the part of human body corresponding to a pixel value, and a module for calculating an average radiopharmaceutical activity concentration, which is used to average all the effective radioactive uptake area pointed at by said quantitative two-dimensional radioactive uptake activity image, and perform volume normalization and decay time correction to figure out the average radiopharmaceutical activity concentration absorbed in the subject, which is a SUV normalization coefficient used to calculate a SPETOMOGRAPHIC quantitative tomography image.

9. The system according to claim 8, wherein said module for calculating an effective radioactive uptake area comprises:

a first submodule, which is used to segment all areas corresponding to the radioactive uptake site of human body in said average image by an image segmentation method based on thresholds or texture features, a second submodule, which is used to detect a pre-defined invalid radioactive uptake area in said average image by a deep-learning or machine-learning algorithm, and a third submodule, which is used to segment all the detected invalid radioactive uptake areas by a level set segmentation method or a deep-learning-based segmentation method, and set a pixel value corresponding to said invalid radioactive uptake area to 0 or an average value of surrounding areas in said average image, thereby obtain the effective radioactive uptake region in said average image.

10. The system according to claim 8, wherein said module for calculating a quantitative two-dimensional radioactive uptake activity image comprises:

a fourth submodule for correcting the attenuation coefficient of human body, wherein a SPETOMOGRAPHIC systemic plain film image and a local TOMOGRAPHIC tomographic image of a subject, and a three-dimensional attenuation coefficient chart based on digital human model are applied to jointly perform image registration, and then the average linear attenuation coefficient corresponding to all effective radioactive uptake areas in the subject is obtained, a fifth submodule for correcting the detection efficiency, wherein types of the SPETOMOGRAPHIC acquisition device and collimator are read from a Dicom data file header information of said SPETOMOGRAPHIC systemic plain film image, and used them to calculate gamma photon detection efficiency, and then the pixel value of the SPETOMOGRAPHIC systemic plain film image is divided by the gamma photon detection efficiency, to figure out the number of gamma photons cumulatively emitted from corresponding parts of human body, and a sixth submodule for performing normalization correction of acquisition time, wherein acquisition time of the systemic plain film image and the SPETOMOGRAPHIC tomographic image from the Dicom data file header information of the subject's SPETOMOGRAPHIC systemic plain film image is read, then a normalization calculation is performed on the number of gamma photons obtained, and the quantitative two-dimensional radioactive uptake activity image is figured out after averaging the three-dimensional spatial distribution of the radioactive uptake activity of each part of the human body corresponding to said average image in the anteroposterior direction.

* * * * *